(12) United States Patent
Mitsuhashi et al.

(10) Patent No.: US 7,157,231 B2
(45) Date of Patent: Jan. 2, 2007

(54) METHOD OF EVALUATING USEFUL CATTLE

(75) Inventors: Tadayoshi Mitsuhashi, Ibaraki (JP); Koichi Chikuni, Ibaraki (JP)

(73) Assignee: Incorporated Administrative Agency National Agriculture and Bio-oriented Research Organization, Tsukuba (JP)

( * ) Notice: Subject to any disclaimer, the term of this patent is extended or adjusted under 35 U.S.C. 154(b) by 405 days.

(21) Appl. No.: 10/471,599

(22) PCT Filed: Jun. 27, 2001

(86) PCT No.: PCT/JP01/05502

§ 371 (c)(1),
(2), (4) Date: Sep. 23, 2003

(87) PCT Pub. No.: WO02/077279

PCT Pub. Date: Oct. 3, 2002

(65) Prior Publication Data

US 2005/0138679 A1     Jun. 23, 2005

(30) Foreign Application Priority Data

Mar. 23, 2001   (JP)   ............................. 2001-084254

(51) Int. Cl.
*C12Q 1/68*     (2006.01)
*C07H 21/02*   (2006.01)
*C07H 21/04*   (2006.01)

(52) U.S. Cl. .................. 435/6; 435/91.2; 536/23.5

(58) Field of Classification Search .................. None
See application file for complete search history.

(56) References Cited

FOREIGN PATENT DOCUMENTS

JP          10-136985          5/1998

OTHER PUBLICATIONS

Schlee, P. Influence of growth-hormone genotypes on breeding values of Simmental bulls. Jul. 1994, Journal of Animal Breeding and Genetics. vol. 111, pp. 253-256.*
Sorensen, P. Polymoprhism in the Bovine Growth Hormone Gene Affects Endocrine Release in Dairy Calves. Jan. 2002, Journal of Dairy Science. vol. 85, pp. 1887-1893.*
Tadayoshi Mihashi et al.: "Kuroke washu seicho hormone idenshi, dai 5 exon no takei to seisansei tono kankei" Nippon Chikusan Gakkai Taikai Kouen Youshi, vol. 94$^{th}$, p. 204 1998 (with English translation).

Yasuaki Yasuda et al.: "Shimaneken ni okeru ushi seichou hormone idenshi no takei ni tsuite (No. 1)" Shimane Kenritsu Chikusan Shikenjo Kenkyu Hokoku, No. 33, pp. 17-19 2000 (with English translation).
Hiroyuki Kataoka et al.: "Okayamaken no kuroke washu ni okeru ushi seichou hormone idenshi no takei to sanniku-sei" Okayama Sougou Chikusan Center Kenkyu Houkoku, No. 11, pp. 1-3 2000 (English translation).
Yasuyuki Fukumoto et al.: "Ushi seichou hormone idenshi no takei ga kuroke washu edaniku seiseki ni oyobosu eikyou" Nippon Chikusan Gakkai Taikai Kouen Youshi, vol. 94$^{th}$, p. 205 1998 (with English translation).
Kouichi Chikuni: "Ushi seichou hormone idenshi no takei to deizai keishitsu" Dobutsu Iden Kenky Zasshi, vol. 26, No. 2, pp. 61-67 1998 (with English translation).
Koichi Chikuni et al.: "Wagyu ni oite miidasareta seichou hormone idenshi no takei" Anim. Sci. Technol., vol. 65, No. 4, pp. 340-346 1994 (with English translation).
K. Chikuni et al.: "A simple method for genotyping the bovine growth hormone gene" Animal Genetics, vol. 28, No. 3, pp. 230-232 1997.
Y.J. Choi et al.: "Analysis of restriction fragment length polymorphism in the bovine growth hormone gene related to growth performance and carcass quality of korean native cattle" Meat Science, vol. 45, No. 3, pp. 405-410 1997.
M. Falaki, et al., "Relationships of Polymorphisms for Growth Hormone and Growth Hormone Receptor Genes with Milk Production Traits for Italian Holstein-Friesian Bulls", Journal of Dairy Science, vol. 79, No. 8, pp. 1446-1453 1996.
Jianbo Yao, et al., "Sequence Variations in the Bovine Growth Hormone Gene Characterized by Single-Strand Conformation Polymorphism (SSCP) Analysis and Their Association with Milk Production Traits in Holsteins", GENETICS, vol. 144, pp. 1809-1816 1996.
C Hecht, et al., "Variants within the 5'-flanking region and the intron I of the bovine growth hormone gene", Animal Genetics, vol. 27, pp. 329-332 1996.
S Høj, et al., "Growth hormone gene polymorphism associated with selection for milk fat production in lines of cattle", Animal Genetics, vol. 24, pp. 91-96 1993.
A. Lagziel, et al., "Association Between SSCP Haplotypes at the Bovine Growth Hormone Gene and Milk Protein Percentage", GENETICS, vol. 142, pp. 945-951 1996.

* cited by examiner

*Primary Examiner*—Ram Shukla
*Assistant Examiner*—Amanda Shaw
(74) *Attorney, Agent, or Firm*—Oblon, Spivak, McClelland, Maier & Neustadt, P.C.

(57)   ABSTRACT

A method that comprises analyzing codon types encoding amino acids at positions 127 and/or 172 of the amino acid sequence of the bovine growth hormone, and evaluating the growth ability and/or the ability to accumulate fat in the muscle of cattle based on the analytical results.

8 Claims, 1 Drawing Sheet

METHOD OF EVALUATING USEFUL CATTLE

TECHNICAL FIELD

The present invention relates to a method for evaluating cattle using genetic polymorphism of the growth hormone, and the growth ability and the ability to accumulate fat in the muscle of cattle.

BACKGROUND ART

Selective breeding of beef sires has been conventionally conducted with a great deal of cost and time. Specifically, the genetic ability of potential sires has been evaluated (progeny test) by selecting bulls and cows based on pedigree information and estimated capabilities, crossing them to produce potential sires, inseminating 7 to 16 cows using the sperm of the potential sires, fattening the resulting calves until they are 21 to 24 months old, and then slaughtering the cattle. However, in spite of such high costs and lengthy time spent for evaluation, cases are often found where potential sires do not possess genetic ability sufficient for the application.

Further, other cases are often found where although fattening farms that fatten and deliver cattle purchase feeder cattle hoping they would produce high-grade beef based on pedigree information, the farms are unable to obtain expected marginal profits, because high-grade beef is not produced.

As described above, useful and available information in addition to pedigree information is required in the field of preliminary selection of sires and selection of feeder cattle.

In the meantime, it has been shown that there is a significant correlation between the growth and texture of beef cattle, and growth hormone levels in blood. Moreover, growth hormone levels in blood are thought to have an effect of promoting the release of accumulated fat from adipose tissue.

The bovine growth hormone gene is composed of 5 exons (portions to be translated into amino acids). Three nucleotide substitutions have been found in the 5$^{th}$ exon, of which two nucleotide substitutions have been shown to be non-conservative substitutions accompanying changes in the amino acid. The non-conservative substitution means that a nucleotide is substituted so as to encode another amino acid differing from the original amino acid. It was reported that a substitution in the vicinity of the 3' side of the gene of these two nucleotide substitutions contains a genotype, which is currently thought to be present only in Japanese black cattle and Japanese brown cattle (Koichi CHIKUNI et al., Nihon Chikusan Gakkaiho, 65, 340–346, 1994). Furthermore, a method for determining a genotype resulting from a nucleotide mutation in the above bovine growth hormone is known (JP Patent Publication (Kokai) No. 10-136985 A).

However, no effective determination method for selective cattle breeding, for determining the correlation between the genotype of the bovine growth hormone and beef phenotype, has yet been reported.

SUMMARY OF THE INVENTION

An object of the present invention is to provide a method for evaluating useful cattle for selective cattle breeding.

As a result of intensive studies to solve the above problems, the present invention has been developed based on the findings that there is a static significance between the codon types of alleles of amino acids at positions 127 and/or 172 in exon 5 of the bovine growth hormone gene, and the growth ability and the ability to accumulate fat in the muscle of cattle. Therefore, it has been found that elite beef cattle can be selected and chosen based on the genetic information.

Specifically, the present invention is a method for evaluating cattle, which comprises analyzing the codon types encoding amino acids at positions 127 and/or 172 of the amino acid sequence of the bovine growth hormone, and evaluating the growth ability and/or the ability to accumulate fat in the muscle of cattle based on the analytical results. Examples of a codon type encoding amino acid at position 127 include GTG/GTG (homo), GTG/CTG (hetero) and CTG/CTG (homo). The codon types encoding the amino acid at position 172 include ACG/ACG (homo), ACG/ATG (hetero) and ATG/ATG (homo). Further, in the method of the present invention, the growth ability of cattle is measured based on body weight gain per day, and the ability to accumulate fat in muscle is measured based on beef marbling score or crude fat content. Moreover, the above codon analysis can be achieved by amplifying genes containing DNAs that encode the above amino acids at positions 127 and/or 172, and analyzing polymorphism of the thus amplified products.

The present invention will be described in detail as follows. This specification includes the content as disclosed in the specification and/or drawings of the Japanese Patent Application No. 2001-84254, from which the present application claims a priority.

The present invention provides as DNA markers the polymorphism of the 5$^{th}$ exon of the bovine growth hormone gene for selective breeding, which is beneficial for cattle production.

Examples of cattle breeds to be evaluated by the present invention include, but are not specifically limited as long as they are bred as beef cattle, Horstein, Hereford, Angus, Japanese Brown, Japanese Black, Simmental, Jersey, Ayrshire, Brown Swiss and Guernsey cattle. The present invention is particularly useful for evaluating Japanese Black cattle.

In the present invention, the bovine growth hormone gene (SEQ ID NO: 5) can be used as a gene for detecting polymorphism. Examples of sources from which genes are collected are not specifically limited. For example, a gene can be collected from muscle, various organs, seminal fluid etc. Any method that can be used by a person skilled in the art may be used as a method for preparing genes (for example, a phenol-chloroform method).

The bovine growth hormone consists of 191 amino acids (SEQ ID NO: 6), wherein two non-conservative nucleotide substitutions are present at positions 127 and 172, where they are represented by codon (unit for amino acid conversion). Among the substitutions, a nucleotide substitution (ATG) corresponding to the substitution (methionine) at amino acid 172 currently is only found in Japanese Black cattle and Japanese Brown cattle. Further, methionine type at amino acid 172 has been found only for valine type of the substitution at amino acid 127 (leucine or valine) (nucleotide types are CTG and GTG, respectively). Accordingly, there are 3 genotypes in the bovine growth hormone peptide because of the nucleotide substitutions at the above two positions. Specifically, the genotype is any one of type A (Leu$^{127}$-Thr$^{172}$), type B (Val$^{127}$-Thr$^{172}$) and type C (Val$^{127}$-Met$^{172}$). Table 1 shows the relationship between each of these genotypes and nucleotide substitutions.

TABLE 1

| Genotype | Codon of amino acid at position 127 | Codon of amino acid at position 172 |
|---|---|---|
| A | CTG (Leu) | ACG (Thr) |
| B | GTG (Val) | ACG (Thr) |
| C | GTG (Val) | ATG (Met) |

According to the present invention, cattle having advantageous genotypes can be evaluated based on the correlation between differences (genetic polymorphism) in codon type of amino acid at position 127, amino acid at position 172, or both amino acids existing in exon 5 of the bovine growth hormone gene as shown in Table 1, and the growth ability, the ability to accumulate fat in the muscle of cattle or both abilities. As criteria for evaluation, codon types of the amino acid at position 127 used herein are 3 types of, or a part of GTG/GTG (homo), GTG/CTG (hetero) and CTG/CTG (homo), and codon types of the amino acid at position 172 used herein are 3 types of or a part of ACG/ACG (homo), ACG/ATG (hetero) and ATG/ATG (homo).

Genetic polymorphism can be analyzed by amplifying a DNA region encoding the sequence of the amino acid at position 127, the amino acid at position 172, or both amino acids of the amino acid sequence of the bovine growth hormone (existing in exon 5 of the bovine growth hormone gene) by the PCR method using primers, and then subjecting the resulting amplified product to electrophoresis. Thus, the genotypes of amino acids at positions 127 and/or 172 can be determined.

Primers used for the PCR method in the present invention can be suitably designed, as long as they are of a primer set that can be amplified from all the genotypes in a DNA region containing the codons of the amino acids at positions 127 and 172 that are present in exon 5 of the bovine growth hormone gene, primers with which codon polymorphism of the amino acid at position 127 in exon 5 can be detected or primers with which codon polymorphism of the amino acid at position 172 in exon 5 can be detected. These primers can be obtained by normal chemical synthesis, and the size is preferably between approximately 20 and 30 mer, and particularly between 25 and 30 mer.

These primers can be used as a kit for detecting polymorphism containing polymerase, dNTP, buffer and the like.

The reaction process of the PCR method consists of thermal denaturation at 93 to 98° C. for 10 to 60 seconds, annealing at 50 to 65° C. for 10 to 60 seconds, and an extension reaction at 65 to 76° C. for 10 to 240 seconds. Preferably, a cycle consisting of thermal denaturation at 94° C. for 30 seconds, annealing at 60° C. for 45 seconds, and an extension reaction at 72° C. for 45 seconds is repeated 30 to 40 times, and more preferably 35 to 40 times.

Next, the product obtained by the PCR method is analyzed by electrophoresis. This analysis by electrophoresis may be performed according to any standard method. For example, the product is subjected to electrophoresis while applying a voltage of 100 V in TAE buffer gel containing 4% agarose, and then the separated DNA band patterns are analyzed. Accordingly, the genotype can be determined.

In the present invention, the above genotypes are classified by every portion in which a nucleotide substitution is present in the genotype of codon 127 and that of codon 172. The study of how the possession of each genotype leads to the acquisition of the growth ability or the ability to accumulate fat enables the evaluation of the growth ability and the ability to accumulate fat in the muscle of cattle which differ in the bovine growth hormone genotype. In this case, body weight gain per day (DG: the amount of body weight gain per day (kg/day)) can be used as an indicator of the growth ability of cattle (also referred to as weight gain ability), and BMS (beef marbling score) or crude fat content can be used as an indicator of the ability to accumulate fat in muscle. These values can be the basis for evaluating elite cattle. For example, in the case where types of codon 127, BMS and the like and DG are compared among GTG/GTG (homo), GTG/CTG (hetero) and/or CTG/CTG (homo). Further, in the case where types of codon 172, BMS and the like and DG are compared among ACG/ACG (homo), ACG/ATG (hetero) and/or ATG/ATG (homo). When there is a statistically significant difference in mean values between any compared groups, cattle having the codon type showing the significant difference can be evaluated as elite cattle. Therefore, useful beef cattle with high-grade texture can be selected based on the above evaluation.

Here, the term "ability to accumulate fat in muscle" refers to "genetic ability to produce marbled meat." The term "marbling" refers to the accumulation of fat in muscle, particularly within the red meat of longissimus muscle, such that white fat is so accumulated in red meat to form marbling. This is mainly determined based on "beef marbling." In the present invention, the standards of JAPAN MEAT GRADING ASSOCIATION are normally employed.

Further, the term "crude fat content" refers to fat weight, which is obtained by the following official method described in A.O.A.C. (Association of Official Method of Analytical Chemists): Official method of analysis (14th edition), pp. 159–169, Association of Official Method of Analytical Chemists, Inc., Arlington, Va. 2209 U.S.A., 1984. Crude fat content can be determined as follows. Specifically, meat is minced to a 3 mm thickness using a mincer, and then mixed. A few grams of the minced meat are weighed out, and then freeze-dried for approximately 48 hours to remove water. Then, the fat is extracted into a flask that has been weighed using diethylether by a fat extractor (normally, a Soxhlet extractor). After extraction, the diethylether is evaporated, the flask containing only fat is weighed, and then by subtracting the flask weight, the fat weight is obtained.

BEST MODE OF CARRYING OUT THE INVENTION

Figure 1:
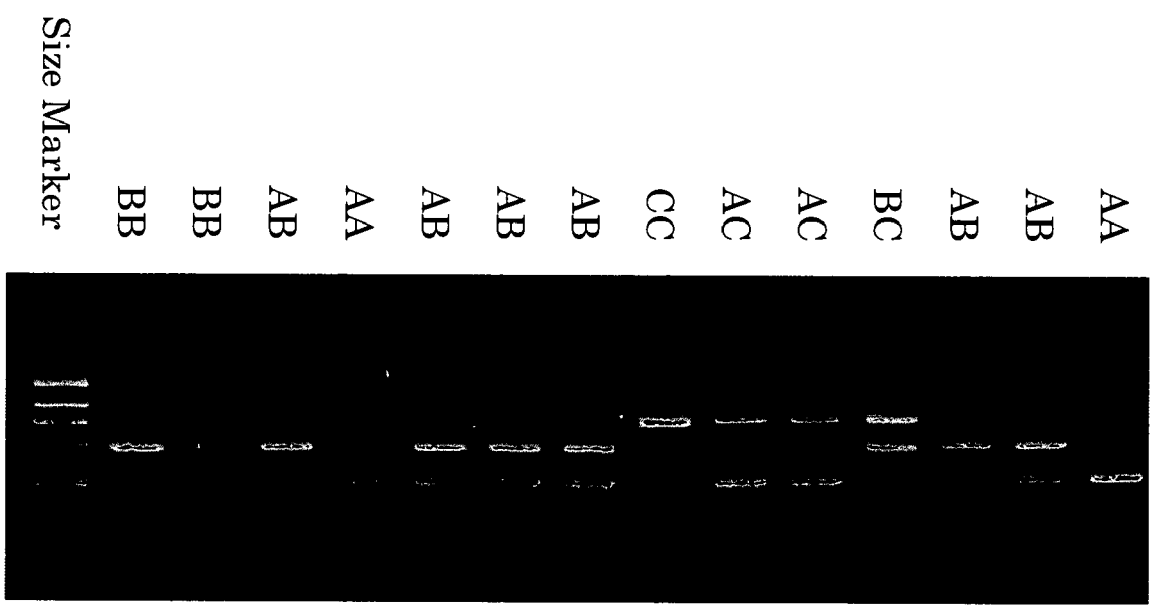
FIG. 1 is a photograph showing the 5 exon polymorphisms of the bovine growth hormone gene, as measured by electrophoresis. A, B and C, respectively show type A (Leu$^{127}$-Thr$^{172}$), type B (Val$^{127}$-Thr172 and type C (Val$^{127}$-Met$^{172}$).

The present invention will be hereafter described by way of examples. However, the technical scope of the present invention is not limited by these examples.

EXAMPLE 1

Analysis of Genotypes Existing on the 5$^{th}$ Exon of the Growth Hormone

To elucidate whether or not a genotype has a significant relationship with production trait, it is required to conduct analysis under specific environmental conditions including nutrition, feeding and the like. Hence, approximately 180 Japanese Black cattle (progeny test cattle, Livestock Improvement Association of Japan), which were of a population consisting of those bred under the same feeding conditions and slaughtered at the same age in months, were subjected to this analysis. Genotyping was performed by the following PCR method.

(1) Primer

Primers for exon 4 and exon 5 of the bovine growth hormone gene were synthesized. A pair of primers capable of amplifying all the genotypes was of GH4F and GH5R.

```
GH4F:
5'-tctatgagaagctgaaggacctggaggaa-3'  (SEQ ID NO: 1)
GH5R:
5'-ccagaatagaatgacacctactcagacaat-3' (SEQ ID NO: 2)
```

A 656-bp amplification product was obtained by the PCR method using the primers. Further, as a mutation-specific primer, a primer having on its 3' end a mutation site corresponding to the codon of amino acid at position 127 in exon 5 was designated as GHAR. A 347-bp amplification product was obtained using the primer. Further, as a mutation-specific primer, a primer having on its 3' end a mutation site corresponding to the codon of amino acid at position 172 in exon 5 was designated as GHABR. A 483-bp amplification product was obtained using the primer.

```
GHAR:  5'-cgggggtgccatcttccag-3'   (SEQ ID NO: 3)
GHABR: 5'-atgaccctcaggtacgtctccgt-3' (SEQ ID NO: 4)
```

(2) PCR Method

20 µl of a reaction solution was prepared by adding 0.5 units of Taq polymerase (PERKIN ELMER) to 100 ng of a template DNA, 200 µM dNTPs, 0.4 µM primers (GH4F and GH5R) and 0.1 µM primers (GHAR and GHABR). A cycle consisting of thermal denaturation at 94° C. for 30 seconds, annealing at 60° C. for 45 seconds, and extension reaction at 72° C. for 45 seconds was repeated 40 times using a PCR system (PERKIN ELMER).

(3) Analysis by Electrophoresis

Next, the products obtained by the above PCR method were analyzed by electrophoresis. The electrophoresis apparatus used herein was a Mupid (COSMO BIO). Gel for electrophoresis (4% agarose, TAE buffer) was prepared in a gel tray, and DNA amplified by PCR was added to the tray. Subsequently, electrophoresis was performed while applying a voltage of 100 V. Then, the separated DNA band patterns were stained by a standard method, and then analyzed. φx174 DNA/Hinc II digest was used as a DNA molecular marker.

The results are shown in FIG. 1. As shown in FIG. 1, type AA was detected at a position of 347 bp, type BB at a position of 483 bp and type CC at a position of 656 bp, as a single band, respectively.

Based on the obtained results, the subject cattle were classified into 2 groups according to the codon types of amino acid at position 127: 1) GTG/GTG (homo), and 2) GTG/CTG (hetero) and CTG/CTG (homo). The subject cattle were classified into 2 groups according to the codon types of amino acid at position 172: 1) ACG/ACG (homo), and 2) ACG/ATG (hetero) and ATG/ATG (homo).

EXAMPLE 2

Measurement of Body Weight Gain Per Day and Beef Marbling Score in Each Codon Type Next, for cattle in the groups of each codon type as set in Example 1, body weight gain per day as an indicator of the growth ability of cattle was measured and beef marbling was scored as an indicator of ability to accumulate fat in muscle. The results are shown in Tables 2 and 3.

TABLE 2

| | Codon type of amino acid at position 127 | | |
|---|---|---|---|
| | GTG/GTG (homo) BB, BC, CC | GTG/CTG (hetero) CTG/CTG (homo) AA, AB, AC | Significance in difference between mean values |
| BMS | 4.46 ± 0.22 | 3.85 ± 0.16 | 0.023 |
| DG | 0.87 ± 0.013 | 0.88 ± 0.010 | 0.549 |

TABLE 3

| | Codon type of amino acid at position 172 | | |
|---|---|---|---|
| | ACG/ACG (homo) AA, AB, BB | ACG/ATG (hetero) ATG/ATG (homo) AC, BC, CC | Significance in difference between mean values |
| BMS | 3.84 ± 0.17 | 4.35 ± 0.19 | 0.054 |
| DG | 0.89 ± 0.010 | 0.86 ± 0.011 | 0.035 |

As shown in Table 2, the codon types of the allele of amino acid at position 127 were classified into a type wherein the codon type is GTG/GTG (homo, Val/Val), and a type wherein the codon type is GTG/CTG (hetero, Val/Leu) or CTG/CTG (homo, Leu/Leu). Then, the codon types were compared for the beef marbling score and body weight gain per day. For beef marbling score, a significant difference was found between the values of the two types. However for body weight gain per day, no significant difference was found between the two types. Accordingly, differences in codon type of amino acid at position 127 made differences in beef marbling clear. Moreover, it was shown that differences in codon type do not cause any problems in the body weight of individual cattle. These results revealed that cattle having the codon type of amino acid at position 127 of GTG/GTG (homo, Val/Val), and genotype BB, BC or CC corresponding to the codon type are superior to the other type of cattle in ability to accumulate fat in muscle and are equivalent to the same in growth ability.

As shown in Table 3, the codon types of amino acid at position 172 were classified into a type wherein the codon type is ACG/ACG (homo, Thr/Thr), and a type wherein the codon type is ACG/ATG (hetero, Thr/Met) or ATG/ATG (homo, Met/Met). Then, the codon types were compared for the beef marbling score and body weight gain per day. For the beef marbling score, a difference tended to be found between the values of the two types (P<0.10). For body weight gain per day, a significant difference (P<0.05) was found between the values of the two types. Accordingly, differences in codon type of amino acid at position 172 made differences in growth ability clear, but it was shown that the beef marbling score of individual cattle with good growth ability tended to be low. These results revealed that cattle having the codon type of amino acid at position 172 of ACG/ACG (homo), and genotype AA, AB or BB corresponding to the codon type are superior in growth ability to the other type of cattle.

All publications, patents and patent applications cited herein are incorporated herein by reference in their entirety.

INDUSTRIAL APPLICABILITY

The present invention provides a method for evaluating cattle. According to the method of the present invention, the growth ability and the ability to accumulate fat in the muscle of cattle can be evaluated by analyzing the codon types of amino acids at positions 127 and/or 172 of the bovine growth hormone gene, so that useful selective breeding can be performed.

Sequence Listing Free Text
 SEQ ID NO:1: Synthetic DNA
 SEQ ID NO:2: Synthetic DNA
 SEQ ID NO:3: Synthetic DNA
 SEQ ID NO:4: Synthetic DNA

The invention claimed is:

1. A method for evaluating Japanese Black cattle for ability to accumulate fat in muscle, which comprises: obtaining a sample of nucleic acid from the Japanese Black cattle, analyzing the nucleic acid for a codon encoding an amino acid at position 127 of the amino acid sequence of the bovine growth hormone of the Japanese Black cattle, and evaluating whether the Japanese Black cattle are excellent in terms of ability to accumulate fat in muscle based on said analyzing, wherein the Japanese Black cattle having the codon type of GTG/GTG (homo) encoding amino acid at position 127 are evaluated as being excellent in terms of ability to accumulate fat in muscle.

2. The method for evaluating Japanese Black cattle according to claim 1, wherein the ability to accumulate fat in muscle is measured based on beef marbling score or crude fat content.

3. The method for evaluating Japanese Black cattle according to claim 1, wherein the nucleic acid is analyzed by amplifying a gene that encodes the bovine growth hormone, and analyzing the amino acid of position 127.

4. A method for evaluating Japanese Black cattle for growth ability, which comprises: obtaining a sample of nucleic acid from the Japanese Black cattle, analyzing the nucleic acid for a codon encoding an amino acid at position 172 of the amino acid sequence of the bovine growth hormone of the Japanese Black cattle, and evaluating whether the Japanese Black cattle are excellent in terms of growth ability based on said analyzing wherein the Japanese Black cattle having the codon type of ACG/ACG (homo) encoding amino acid at position 172 are evaluated as being excellent in terms of growth ability.

5. The method for evaluating Japanese Black cattle according to claim 4, wherein the growth ability of the Japanese Black cattle is measured based on body weight gain per day.

6. The method for evaluating Japanese Black cattle according to claim 4, wherein the nucleic acid is analyzed by amplifying a gene that encodes bovine growth hormone, and analyzing the amino acid of position 172.

7. A method for breeding elite Japanese Black cattle having excellent ability to accumulate fat in muscle, which comprises: obtaining a sample of nucleic acid from the Japanese Black cattle, analyzing the nucleic acid for a codon encoding an amino acid at position 127 of the amino acid sequence of the bovine growth hormone of the Japanese Black cattle; selecting Japanese Black cattle having the codon of GTG/GTG (homo) encoding amino acid at position 127 based on said analyzing; and breeding by crossing the selected cattle.

8. A method for breeding elite Japanese Black cattle having excellent growth ability, which comprises: obtaining a sample of nucleic acid from the Japanese Black cattle, analyzing the nucleic acid for a codon encoding an amino acid at position 172 of the amino acid sequence of the bovine growth hormone of the Japanese Black cattle selecting Japanese Black cattle having the codon of ACG/ACG (homo) encoding amino acid at position 172 based on said analyzing; and breeding by crossing the selected cattle.

* * * * *

```
                             SEQUENCE LISTING

<160> NUMBER OF SEQ ID NOS: 6

<210> SEQ ID NO 1
<211> LENGTH: 29
<212> TYPE: DNA
<213> ORGANISM: Artificial Sequence
<220> FEATURE:
<223> OTHER INFORMATION: synthetic DNA

<400> SEQUENCE: 1
tctatgagaa gctgaaggac ctggaggaa                                       29

<210> SEQ ID NO 2
<211> LENGTH: 30
<212> TYPE: DNA
<213> ORGANISM: Artificial Sequence
<220> FEATURE:
<223> OTHER INFORMATION: synthetic DNA

<400> SEQUENCE: 2
ccagaataga atgacaccta ctcagacaat                                      30

<210> SEQ ID NO 3
<211> LENGTH: 20
<212> TYPE: DNA
<213> ORGANISM: Artificial Sequence
<220> FEATURE:
<223> OTHER INFORMATION: synthetic DNA

<400> SEQUENCE: 3 cgggggtgc catcttccag                                                  20

<210> SEQ ID NO 4
<211> LENGTH: 23
<212> TYPE: DNA
<213> ORGANISM: Artificial Sequence
<220> FEATURE:
<223> OTHER INFORMATION: synthetic DNA

<400> SEQUENCE: 4
atgaccctca ggtacgtctc cgt                                             23

<210> SEQ ID NO 5
<211> LENGTH: 2206
<212> TYPE: DNA
<213> ORGANISM: Bos Taurus
<220> FEATURE:
<221> NAME/KEY: misc_feature
<222> LOCATION: (76)..(78)
<223> OTHER INFORMATION: n is g, a, t, or c

<400> SEQUENCE: 5
```

-continued

| | |
|---|---|
| aaaacctatg gggtgggctc tcaagctgag accctgtgtg cacagccctc tggctggtgg | 60 |
| cagtggagac gggatnnnat gacaagcctg ggggacatga ccccagagaa ggaacgggaa | 120 |
| caggatgagt gagaggaggt tctaaattat ccattagcac aggctgccag tggtccttgc | 180 |
| ataaatgtat agagcacaca ggtgggggga aagggagaga gagaagaagc cagggtataa | 240 |
| aaatggccca gcagggacca attccaggat cccaggaccc agttcaccag acgactcagg | 300 |
| gtcctgtgga cagctcacca gctatgatgg ctgcaggtaa gctcgctaaa atcccctcca | 360 |
| ttcgcgtgtc ctaaagggt aatgcggggg gccctgccga tggatgtgtt cagagctttg | 420 |
| ggctttaggg cttccgaatg tgaacatagg tatctacacc cagacatttg gccaagtttg | 480 |
| aaatgttctc agtccctgga gggaagggta ggtgggggct ggcaggagat caggcgtcta | 540 |
| gctccctggg gccctccgtc gcggcctcc tggtctctcc ctaggcccc ggacctccct | 600 |
| gctcctggct ttcgccctgc tctgcctgcc ctggactcag gtggtgggcg ccttcccagc | 660 |
| catgtccttg tccggcctgt ttgccaacgc tgtgctccgg gctcagcacc tgcatcagct | 720 |
| ggctgctgac accttcaaag agtttgtaag ctcccgaggg atgcgtccta ggggtgggga | 780 |
| ggcaggaagg ggtgaatcca cacccctcc acacagtggg aggaaactga ggagttcagc | 840 |
| cgtattttat ccaagtaggg atgtggttag gggagcagaa acggggtgt gtgggtggg | 900 |
| gagggttccg aataaggcgg ggaggggaac cgcgcaccag cttagacctg ggtgggtgtg | 960 |
| ttcttccccc aggagcgcac ctacatcccg gagggacaga gatactccat ccagaacacc | 1020 |
| caggttgcct tctgcttctc tgaaaccatc ccggcccca cgggcaagaa tgaggcccag | 1080 |
| cagaaatcag tgagtggcaa cctcggaccg aggagcaggg gacctccttc atcctaagta | 1140 |
| ggctgcccca gctctccgca ccgggcctgg ggcggcctc tccccgaggt ggcggaggtt | 1200 |
| gttggatggc agtggaggat gatggtgggc ggtggtggca ggaggtcctc gggcagaggc | 1260 |
| cgaccttgca gggctgcccc aagcccgcgg cacccaccga ccaccatct gccagcagga | 1320 |
| cttggagctg cttcgcatct cactgctcct catccagtcg tggcttgggc cctgcagtt | 1380 |
| cctcagcaga gtcttcacca acagcttggt gtttggcacc tcggaccgtg tctatgagaa | 1440 |
| gctgaaggac ctggaggaag gcatcctggc cctgatgcgg gtggggatgg cgttgtgggt | 1500 |
| cccttccatg ctggggggcca tgcccgccct ctcctggctt agccaggaga atgcacgtgg | 1560 |
| gcttggggag acagatccct gctctctccc tctttctagc agtccagcct tgacccaggg | 1620 |
| gaaacctttt cccctttga aacctccttc ctcgccctc tccaagcctg taggggaggg | 1680 |
| tggaaaatgg agcgggcagg agggagctgc tcctgagggc ccttcggcct ctctgtctct | 1740 |
| ccctcccttg gcaggagctg gaagatggca cccccgggc tgggcagatc ctcaagcaga | 1800 |
| cctatgacaa atttgacaca aacatgcgca gtgacgacgc gctgctcaag aactacggtc | 1860 |
| tgctctcctg cttccggaag gacctgcata gacgagac gtacctgagg gtcatgaagt | 1920 |
| gccgccgctt cggggaggcc agctgtgcct tctagttgcc agccatctgt tgtttgcccc | 1980 |
| tcccccgtgc cttccttgac cctggaaggt gccactccca ctgtcctttc ctaataaaat | 2040 |
| gaggaaattg catcgcattg tctgagtagg tgtcattcta ttctgggggg tggggtgggg | 2100 |
| caggacagca aggggagga ttgggaagac aatagcaggc atgctgggga tgcggtgggc | 2160 |
| tctatgggta cccaggtgct gaagaattga cccggttcct cctggg | 2206 |

<210> SEQ ID NO 6
<211> LENGTH: 191
<212> TYPE: PRT
<213> ORGANISM: Bos taurus

```
<400> SEQUENCE: 6

Ala Phe Pro Ala Met Ser Leu Ser Gly Leu Phe Ala Asn Ala Val Leu
1               5                   10                  15

Arg Ala Gln His Leu His Gln Leu Ala Ala Asp Thr Phe Lys Glu Phe
                20                  25                  30

Glu Arg Thr Tyr Ile Pro Glu Gly Gln Arg Tyr Ser Ile Gln Asn Thr
            35                  40              45

Gln Val Ala Phe Cys Phe Ser Glu Thr Ile Pro Ala Pro Thr Gly Lys
        50                  55                  60

Asn Glu Ala Gln Gln Lys Ser Asp Leu Glu Leu Leu Arg Ile Ser Leu
65                  70                  75                  80

Leu Leu Ile Gln Ser Trp Leu Gly Pro Leu Gln Phe Leu Ser Arg Val
                85                  90                  95

Phe Thr Asn Ser Leu Val Phe Gly Thr Ser Asp Arg Val Tyr Glu Lys
                100                 105                 110

Leu Lys Asp Leu Glu Glu Gly Ile Leu Ala Leu Met Arg Glu Leu Glu
            115                 120                 125

Asp Gly Thr Pro Arg Ala Gly Gln Ile Leu Lys Gln Thr Tyr Asp Lys
            130                 135                 140

Phe Asp Thr Asn Met Arg Ser Asp Asp Ala Leu Leu Lys Asn Tyr Gly
145                 150                 155                 160

Leu Leu Ser Cys Phe Arg Lys Asp Leu His Lys Thr Glu Thr Tyr Leu
                165                 170                 175

Arg Val Met Lys Cys Arg Arg Phe Gly Glu Ala Ser Cys Ala Phe
                180                 185                 190
```